United States Patent
Jung et al.

(10) Patent No.: US 11,399,764 B2
(45) Date of Patent: Aug. 2, 2022

(54) PHRENIC NERVE STIMULATOR, AND SYSTEM AND METHOD FOR MONITORING PHRENIC NERVE STIMULATION

(71) Applicant: Boston Scientific Scimed, Inc., Maple Grove, MN (US)

(72) Inventors: Eugene J. Jung, San Diego, CA (US); Chadi Harmouche, Saint-Laurent (CA)

(73) Assignee: Boston Scientific Scimed, Inc., Maple Grove, MN (US)

( * ) Notice: Subject to any disclaimer, the term of this patent is extended or adjusted under 35 U.S.C. 154(b) by 171 days.

(21) Appl. No.: 16/685,152

(22) Filed: Nov. 15, 2019

(65) Prior Publication Data

US 2020/0077938 A1    Mar. 12, 2020

Related U.S. Application Data

(63) Continuation of application No. PCT/US2018/025878, filed on Apr. 3, 2018.
(Continued)

(51) Int. Cl.
*A61B 5/00* (2006.01)
*A61N 1/04* (2006.01)
(Continued)

(52) U.S. Cl.
CPC ............ *A61B 5/4035* (2013.01); *A61B 5/742* (2013.01); *A61B 5/7405* (2013.01); *A61B 5/746* (2013.01);
(Continued)

(58) Field of Classification Search
CPC .......... A61B 18/02; A61B 2018/00577; A61B 2018/0212; A61B 2562/0219; A61B 2562/0261; A61B 5/08; A61B 5/113; A61B 5/4035; A61B 5/4836; A61B 5/6822; A61B 5/6823; A61B 5/7405; A61B 5/742;
(Continued)

(56) References Cited

U.S. PATENT DOCUMENTS

2002/0188332 A1    12/2002  Lurie et al.
2009/0306638 A1    12/2009  Hillely et al.
(Continued)

OTHER PUBLICATIONS

International Search Report and Written Opinion received for PCT Patent Application No. PCT/US2018/025878, dated Aug. 1, 2018, 14 pages.

*Primary Examiner* — George Manuel
(74) *Attorney, Agent, or Firm* — Faegre Drinker Biddle & Reath LLP

(57) ABSTRACT

A phrenic nerve pacing monitor assembly for a cryogenic balloon catheter system used during a cryoablation procedure, which monitors movement of a diaphragm of a patient, includes a pacing detector and a safety system. The pacing detector directly monitors movement of the diaphragm of the patient to detect when phrenic nerve pacing is occurring. Additionally, the pacing detector generates monitor output based on the movement of the diaphragm of the patient. The safety system receives the monitor output and based at least in part on the monitor output selectively provides an alert when movement of the diaphragm of the patient is atypical. The safety system is configured to provide the alert only while at least one of (i) phrenic nerve pacing is occurring, and (ii) cryoablation is occurring.

14 Claims, 5 Drawing Sheets

Related U.S. Application Data

(60) Provisional application No. 62/517,943, filed on Jun. 11, 2017, provisional application No. 62/515,987, filed on Jun. 6, 2017, provisional application No. 62/507,072, filed on May 16, 2017.

(51) Int. Cl.
*A61B 18/02* (2006.01)
*A61B 18/00* (2006.01)

(52) U.S. Cl.
CPC ............ *A61B 5/7455* (2013.01); *A61B 18/02* (2013.01); *A61N 1/0456* (2013.01); *A61B 5/6822* (2013.01); *A61B 5/6823* (2013.01); *A61B 2018/00577* (2013.01); *A61B 2018/0212* (2013.01); *A61B 2562/0219* (2013.01); *A61B 2562/0261* (2013.01)

(58) Field of Classification Search
CPC .... A61B 5/7455; A61B 5/746; A61N 1/0456; A61N 1/0484; A61N 1/0492; A61N 1/08; A61N 1/3601; A61N 1/36031
See application file for complete search history.

(56) References Cited

U.S. PATENT DOCUMENTS

| | | |
|---|---|---|
| 2012/0197245 A1 | 8/2012 | Burnett et al. |
| 2013/0109994 A1 | 5/2013 | Cho et al. |
| 2013/0296850 A1* | 11/2013 | Olson ................ A61B 18/1492 606/41 |
| 2014/0180278 A1 | 6/2014 | Abboud et al. |
| 2015/0034081 A1* | 2/2015 | Tehrani .............. A61N 1/36139 128/202.13 |
| 2015/0359487 A1* | 12/2015 | Coulombe ........... A61B 5/6856 600/375 |
| 2017/0000422 A1 | 1/2017 | Moturu et al. |

* cited by examiner

PHRENIC NERVE STIMULATOR, AND SYSTEM AND METHOD FOR MONITORING PHRENIC NERVE STIMULATION

CROSS-REFERENCE TO RELATED APPLICATION

This application is a continuation of International Application No. PCT/US2018/025878 filed on Apr. 3, 2018 and entitled PHRENIC NERVE STIMULATOR, AND SYSTEM AND METHOD FOR MONITORING PHRENIC NERVE STIMULATION, which claims the benefit of U.S. Provisional Application No. 62/507,072, filed on May 16, 2017, and entitled "EXTRACORPOREAL PHRENIC NERVE STIMULATOR"; U.S. Provisional Application No. 62/515,987, filed on Jun. 6, 2017, and entitled "EXTRACORPOREAL PHRENIC NERVE STIMULATOR"; and U.S. Provisional Application No. 62/517,943, filed on Jun. 11, 2017, and entitled "SYSTEM AND METHOD FOR MONITORING PHRENIC NERVE PACING". As far as permitted, the contents of International Application No. PCT/US2018/025878 and U.S. Provisional Application Nos. 62/507,072, 62/515,987 and 62/517,943 are incorporated in their entirety herein by reference.

TECHNICAL FIELD

The present disclosure relates to electrophysiology devices and methods. More specifically, the disclosure relates to devices and methods for monitoring phrenic nerve stimulation during cardiac ablation procedures.

BACKGROUND

The phrenic nerve, of which there are two in the human body, stimulates movement of the diaphragm to help facilitate breathing. The phrenic nerve is a nerve that originates in the neck, i.e. from the 3rd, 4th and 5th cervical nerves (C3-C5), and passes down between the lung and heart (near the left atrium) to reach the diaphragm. The phrenic nerve is important for breathing, as it passes motor information to the diaphragm and receives sensory information from it. The phrenic nerve also passes near the superior vena cava, thus making it amenable to pacing. Phrenic nerve pacing (or stimulation) is often performed as part of a cryoballoon ablation procedure or other ablation procedure to inhibit unintended injury to the phrenic nerve.

Certain current phrenic nerve pacing or stimulation techniques utilize an intravascular catheter inserted through the femoral vein near the groin, through the inferior vena cava into the superior vena cava. For example, a steerable diagnostic catheter is often used to stimulate the phrenic nerve. The catheter electrodes are placed near the phrenic nerve, and pacing energy is applied through the catheter electrodes to thus stimulate the phrenic nerve. Although this method is effective, it is also both cumbersome and expensive to perform. Accordingly, there remains a need for improving the ease, reliability and cost-effectiveness of phrenic nerve stimulation to inhibit phrenic nerve paralysis during catheter ablation, e.g., during catheter ablation of atrial fibrillation.

Additionally, it is further desired to provide a phrenic nerve pacing monitoring system that can easily, conveniently, accurately and automatically detect changes in diaphragm movement during an ablation procedure so as to effectively inhibit any potential injury to the phrenic nerve.

SUMMARY

The present invention is directed toward a phrenic nerve pacing monitor assembly for a cryogenic balloon catheter system used during a cryoablation procedure. The phrenic nerve pacing monitor assembly monitors movement of a diaphragm of a patient. In various embodiments, the phrenic nerve pacing monitor assembly includes a pacing detector and a safety system. The pacing detector directly monitors movement of the diaphragm of the patient to detect when phrenic nerve pacing is occurring. Additionally, the pacing detector generates monitor output based on the movement of the diaphragm of the patient. The safety system receives the monitor output and based at least in part on the monitor output selectively provides an alert when movement of the diaphragm of the patient is atypical. The safety system is configured to provide the alert only while at least one of (i) phrenic nerve pacing is occurring, and (ii) cryoablation is occurring.

In some embodiments, the safety system is configured to provide the alert only while both of (i) phrenic nerve pacing is occurring, and (ii) cryoablation is occurring. The design of the pacing detector can be varied. For example, in one embodiment, the pacing detector includes an accelerometer. Alternatively, in another embodiment, the pacing detector includes a strain gauge. Still alternatively, in yet another embodiment, the pacing detector includes a compound muscle action potential (CMAP) signal detector.

In certain embodiments, the pacing detector automatically monitors movement of the diaphragm of the patient, and automatically generates the monitor output based on the movement of the diaphragm of the patient.

The type of alert provided by the safety system can also be varied. For example, in one embodiment, the alert includes an audio alert. Alternatively, in another embodiment, the alert includes a video alert. Still alternatively, in yet another embodiment, the alert includes a haptic alert.

Additionally, in some embodiments, the pacing detector is positioned extracorporeally to the patient.

Further, in certain embodiments, the phrenic nerve pacing monitor assembly further includes an ablation detector that detects when cryoablation is occurring.

The present invention is further directed toward a cryogenic balloon catheter system comprising a balloon catheter, a phrenic nerve stimulator that selectively stimulates a phrenic nerve of the patient, and the phrenic nerve pacing monitor assembly as described above that monitors movement of the diaphragm of the patient. In some embodiments, the phrenic nerve stimulator includes a first electrode and a second electrode that are arranged in a bipolar electrode pair; and a pulse generator that is electrically coupled to the bipolar electrode pair, the pulse generator being configured to transmit stimulatory energy to the bipolar electrode pair. In certain such embodiments, the first electrode is configured to be positioned near vertebra C3-C5 of the patient and the second electrode is configured to be positioned near a front of a shoulder of the patient. Alternatively, in other such embodiments, the first electrode is configured to be positioned extracorporeally near a neck of the patient and the second electrode is configured to be positioned extracorporeally near a shoulder of the patient.

Additionally, the present invention is also directed toward a phrenic nerve pacing monitor assembly for a cryogenic balloon catheter system used during a cryoablation procedure, the phrenic nerve pacing monitor assembly monitoring movement of a diaphragm of a patient, the phrenic nerve pacing monitor assembly including a pacing detector that directly monitors movement of the diaphragm of the patient to detect when phrenic nerve pacing is occurring, the pacing detector generating monitor output based on the movement of the diaphragm of the patient; and a safety system that receives the monitor output and based at least in part on the monitor output selectively terminates the cryoablation procedure when movement of the diaphragm of the patient is atypical, the safety system being configured to terminate the cryoablation procedure only while at least one of (i) phrenic nerve pacing is occurring, and (ii) cryoablation is occurring.

In another application, the present invention is directed toward a method for monitoring movement of a diaphragm of a patient during a cryoablation procedure, the method including the steps of directly monitoring movement of the diaphragm of the patient with a pacing detector to detect when phrenic nerve pacing is occurring; generating monitor output with the pacing detector based on the movement of the diaphragm of the patient; receiving the monitor output with a safety system; and selectively providing an alert with the safety system based at least in part on the monitor output when movement of the diaphragm of the patient is atypical, the safety system being configured to provide the alert only while at least one of (i) phrenic nerve pacing is occurring, and (ii) cryoablation is occurring.

In still another application, the present invention is directed toward a method for monitoring movement of a diaphragm of a patient during a cryoablation procedure, the method including the steps of directly monitoring movement of the diaphragm of the patient with a pacing detector to detect when phrenic nerve pacing is occurring; generating monitor output with the pacing detector based on the movement of the diaphragm of the patient; receiving the monitor output with a safety system; and selectively terminating the cryoablation procedure with the safety system based at least in part on the monitor output when movement of the diaphragm of the patient is atypical, the safety system being configured to terminate the cryoablation procedure only while at least one of (i) phrenic nerve pacing is occurring, and (ii) cryoablation is occurring.

In another application, the present invention is directed toward a phrenic nerve stimulator for providing electrical stimulation to a phrenic nerve of a patient, the phrenic nerve stimulator including a first electrode and a second electrode that are arranged in a bipolar electrode pair; and a pulse generator that is electrically coupled to the bipolar electrode pair, the pulse generator being configured to transmit stimulatory energy to the bipolar electrode pair; wherein the first electrode is configured to be positioned near vertebra C3-C5 of the patient and the second electrode is configured to be positioned near a front of a shoulder of the patient.

In yet another application, the present invention is directed toward a phrenic nerve stimulator for providing electrical stimulation to a phrenic nerve of a patient, the phrenic nerve stimulator including a first electrode and a second electrode that are arranged in a bipolar electrode pair; and a pulse generator that is electrically coupled to the bipolar electrode pair, the pulse generator being configured to transmit stimulatory energy to the bipolar electrode pair; wherein the first electrode is configured to be positioned extracorporeally near a neck of the patient and the second electrode is configured to be positioned extracorporeally near a shoulder of the patient.

Additionally, the present invention is further directed toward a method for providing electrical stimulation to a phrenic nerve of a patient, the method including the steps of arranging a first electrode and a second electrode in a bipolar electrode pair; positioning the first electrode near vertebra C3-C5 of the patient; positioning the second electrode near a front of a shoulder of the patient; electrically coupling a pulse generator to the bipolar electrode pair; and transmitting stimulatory energy from the pulse generator to the bipolar electrode pair Further, the present invention is also directed toward a method for providing electrical stimulation to a phrenic nerve of a patient, the method including the steps of arranging a first electrode and a second electrode in a bipolar electrode pair; positioning the first electrode extracorporeally near a neck of the patient; positioning the second electrode extracorporeally near a shoulder of the patient; electrically coupling a pulse generator to the bipolar electrode pair; and transmitting stimulatory energy from the pulse generator to the bipolar electrode pair.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
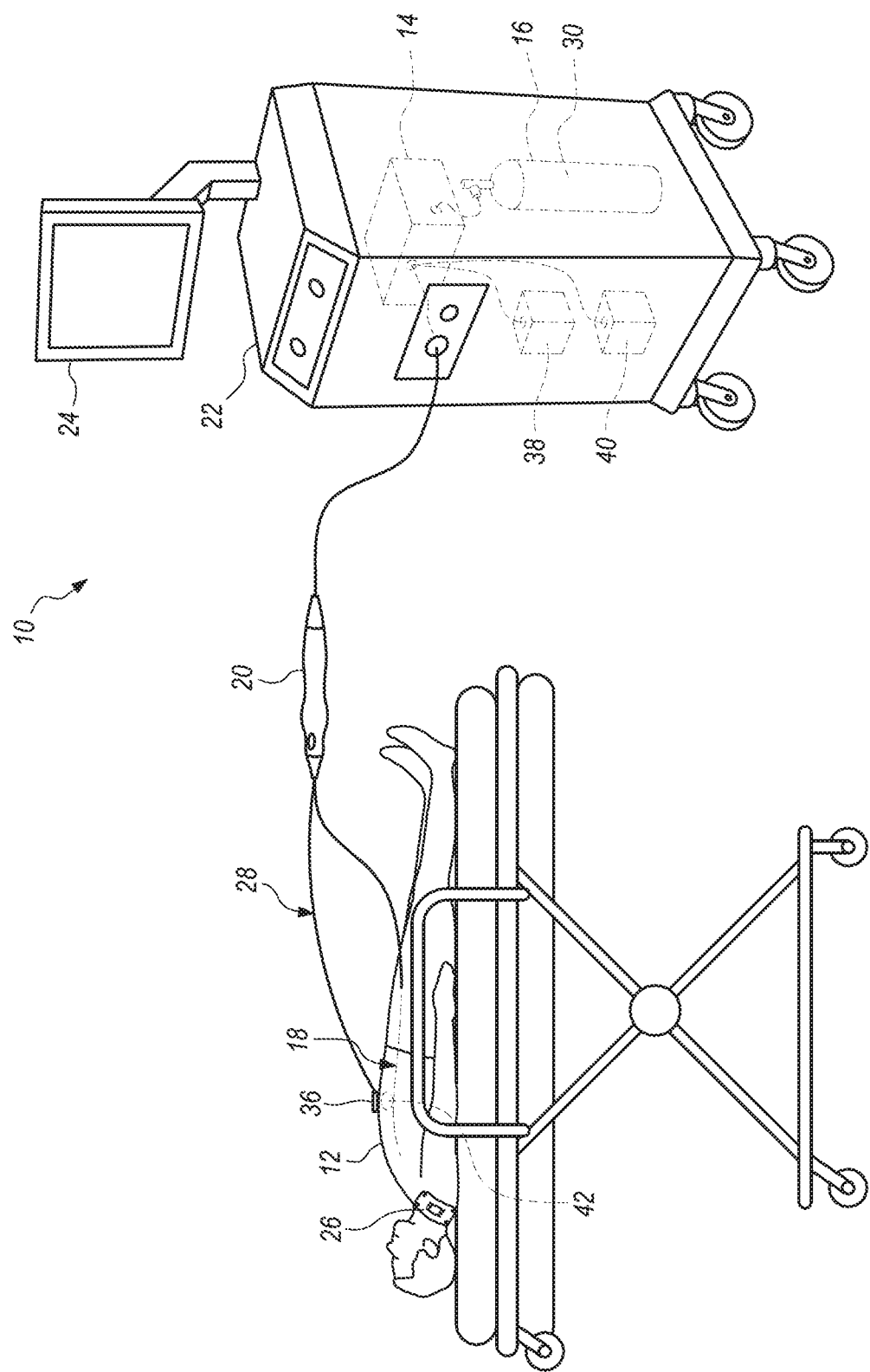
FIG. 1 is a simplified schematic side view illustration of a patient and one embodiment of a cryogenic balloon catheter system including a phrenic nerve stimulator and a phrenic nerve pacing monitor assembly having features of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Embodiments of the present invention are described herein in the context of a phrenic nerve stimulator and a phrenic nerve pacing monitor assembly for use during cardiac ablation procedures. In particular, in various embodiments, the phrenic nerve stimulator is configured to stimulate the phrenic nerve from outside the body, i.e. in an extracorporeal manner, during such an ablation procedure. Additionally, in certain embodiments, the phrenic nerve pacing monitor assembly is configured to determine whether at least one of phrenic nerve pacing and cryoablation, is occurring. Further, based on whether one or both of these processes are occurring, the phrenic nerve pacing monitor assembly can send appropriate signals or alerts to the operator to terminate the cryoablation procedure under certain circumstances.

If diaphragmatic movement slows down during an ablation procedure, it is generally an indication that the phrenic nerve is being adversely affected. In some embodiments, by closely monitoring movement of the diaphragm, a rapid determination of potential damage to the phrenic nerve may help avoid injury to the patient. For example, without proper monitoring of movement of the diaphragm, thermal injury to the phrenic nerve can occur, which can result in nerve paralysis and diaphragmatic impairment that can be associated with temporary or even permanent breathing difficulties. It is appreciated that during phrenic nerve pacing or stimulation, the movement of the diaphragm can be measured in several ways. In other current methods, a physician or other staff member may place a hand on the patient near the stomach to feel the stimulated motion of the diaphragm, or the physician may utilize sensors that measure other parameters that are related to the movement of the diaphragm. These detection methods that are currently being used are often accomplished manually, which can increase the required work of the physician and other staff members. Further, these methods require the operator to manually and/or affirmatively tell the system when detection of changes in diaphragm movement should be initiated in order to inhibit false failures. Thus, the phrenic nerve pacing monitoring system of the present invention that can easily, conveniently, accurately, directly and automatically detect changes in diaphragm movement during an ablation procedure greatly enhances the ability of inhibiting potential thermal injury to the phrenic nerve.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound and laser energy, as nonexclusive examples. The present invention is intended to be effective with any or all of these and other forms of energy.

FIG. 1 is a simplified schematic side view illustration of an embodiment of a medical device 10 for use with a patient 12, which can be a human being or an animal. Although the specific medical device 10 illustrated and described herein pertains to and refers to a cryogenic balloon catheter system 10, it is understood and appreciated that other types of medical devices 10 or systems can equally benefit by the teachings provided herein. For example, in certain nonexclusive alternative embodiments, the present invention can be equally applicable for use with any suitable types of ablation systems and/or any suitable types of catheter systems. Thus, the specific reference herein to use as part of a cryogenic balloon catheter system is not intended to be limiting in any manner.

The design of the cryogenic balloon catheter system 10 can be varied. In certain embodiments, such as the embodiment illustrated in FIG. 1, the cryogenic balloon catheter system 10 can include one or more of a control system 14 (illustrated in phantom), a fluid source 16 (illustrated in phantom), a balloon catheter 18, a handle assembly 20, a control console 22, a graphical display 24, a phrenic nerve stimulator 26, and a phrenic nerve pacing monitor assembly 28 (also sometimes referred to herein as a "pacing monitor assembly").

It is understood that although FIG. 1 illustrates the structures of the cryogenic balloon catheter system 10 in a particular position, sequence and/or order, these structures can be located in any suitably different position, sequence and/or order than that illustrated in FIG. 1. It is also understood that the cryogenic balloon catheter system 10 can include fewer or additional components than those specifically illustrated and described herein.

In various embodiments, the control system 14 is configured to monitor and control the various processes of the ablation procedure. More specifically, the control system 14 can monitor and control release and/or retrieval of a cooling fluid 30 (e.g., a cryogenic fluid) to and/or from the balloon catheter 18. The control system 14 can also control various structures that are responsible for maintaining and/or adjusting a flow rate and/or pressure of the cryogenic fluid 30 that is released to the balloon catheter 18 during the cryoablation procedure. In such embodiments, the cryogenic balloon catheter system 10 delivers ablative energy in the form of cryogenic fluid 30 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive data and/or other information (hereinafter sometimes referred to as "sensor output") from various structures within the cryogenic balloon catheter system 10, and/or can receive data and/or other information (hereinafter sometimes referred to as "monitor output") from the pacing monitor assembly 28. In some embodiments, the control system 14 can receive, monitor, assimilate and/or integrate the sensor output, the monitor output, and/or any other data or information received from any structure within the cryogenic balloon catheter system 10 in order to control the operation of the balloon catheter 18. As provided herein, in various embodiments, the control system 14 can initiate and/or terminate the flow of cryogenic fluid 30 to the balloon catheter 18 based on the sensor output and the monitor output. Still further, or in the alternative, the control system 14 can control positioning of portions of the balloon catheter 18 within the body of the patient 12, and/or can control any other suitable functions of the balloon catheter 18.

The fluid source 16 contains the cryogenic fluid 30, which is delivered to the balloon catheter 18 with or without input from the control system 14 during a cryoablation procedure. Once the ablation procedure has initiated, the cryogenic fluid 30 can be delivered and the resulting gas, after a phase change, can be retrieved from the balloon catheter 18, and can either be vented or otherwise discarded as exhaust. Additionally, the type of cryogenic fluid 30 that is used during the cryoablation procedure can vary. In one non-exclusive embodiment, the cryogenic fluid 30 can include liquid nitrous oxide. However, any other suitable cryogenic fluid 30 can be used. For example, in one non-exclusive alternative embodiment, the cryogenic fluid 30 can include liquid nitrogen.

The design of the balloon catheter 18 can be varied to suit the specific design requirements of the cryogenic balloon catheter system 10. As shown, the balloon catheter 18 is inserted into the body of the patient 12 during the cryoablation procedure. In one embodiment, the balloon catheter 18 can be positioned within the body of the patient 12 using the control system 14. Alternatively, the balloon catheter 18 can be manually positioned within the body of the patient 12 by a healthcare professional (also referred to herein as an "operator"). As used herein, a healthcare professional and/or operator can include a physician, a physician's assistant, a nurse and/or any other suitable person or individual. In certain embodiments, the balloon catheter 18 is positioned within the body of the patient 12 utilizing at least a portion of the sensor output that is received by the control system 14. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue (not shown). While specific reference is made herein to the balloon catheter 18, as noted above, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the cryogenic balloon catheter system 10. In the embodiment illustrated in FIG. 1, the handle assembly 20 is separate from, but in electrical and/or fluid communication with the control system 14, the fluid source 16, the graphical display 24, and the pacing monitor assembly 28. In some embodiments, the handle assembly 20 can integrate and/or include at least a portion of the control system 14 and/or the pacing monitor assembly 26 within an interior of the handle assembly 20. It is understood that the handle assembly 20 can include fewer or additional components than those specifically illustrated and described herein.

In various embodiments, the handle assembly 20 can be used by the operator to initiate and/or terminate the cryoablation process, e.g. start the flow of the cryogenic fluid 30 to the balloon catheter 18 in order to ablate certain targeted heart tissue of the patient 12. In certain embodiments, the control system 14 can override use of the handle assembly 20 by the operator. Stated in another manner, in some embodiments, based at least in part on the monitor output, the control system 14 can terminate the cryoablation process without the operator using the handle assembly 20 to do so.

In the embodiment illustrated in FIG. 1, the control console 22 includes at least a portion of the control system 14, the fluid source 16, the graphical display 24, and the pacing monitor assembly 28. However, in alternative embodiments, the control console 22 can contain additional structures not shown or described herein. Still alternatively, the control console 22 may not include various structures that are illustrated within the control console 22 in FIG. 1. For example, in certain nonexclusive alternative embodiments, the control console 22 does not include the graphical display 24.

In various embodiments, the graphical display 24 is electrically connected to the control system 14 and the pacing monitor assembly 28. Additionally, the graphical display 24 provides the operator of the cryogenic balloon catheter system 10 with information that can be used before, during and after the cryoablation procedure. For example, the graphical display 24 can provide the operator with information based on the sensor output, the monitor output, and any other relevant information that can be used before, during and after the cryoablation procedure. The specifics of the graphical display 24 can vary depending upon the design requirements of the cryogenic balloon catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time, e.g., during an ablation procedure. Further, in various embodiments, the graphical display 24 can include one or more colors, different sizes, varying brightness, etc., that may act as alerts to the operator. Additionally, or in the alternative, the graphical display 24 can provide audio data or information to the operator.

As provided herein, the phrenic nerve stimulator 26 can be utilized to stimulate the phrenic nerves 332A, 332B (illustrated in FIG. 3) from outside the body 334 (illustrated in FIG. 3) of the patient 12, i.e. in an extracorporeal manner. For example, the phrenic nerve stimulator 26 can be utilized to stimulate the phrenic nerves 332A, 332B during a cardiac ablation procedure. The particular design, positioning and functioning of the phrenic nerve stimulator 26 will be described in greater detail herein below.

The design of the pacing monitor assembly 28 can be varied depending upon the design requirements of the cryogenic balloon catheter system 10. In the embodiment illustrated in FIG. 1, the pacing monitor assembly 28 includes one or more of a pacing detector 36, an ablation detector 38, and a safety system 40. Alternatively, the pacing monitor assembly 28 can include additional components or fewer components than those specifically illustrated and described herein.

As described in detail herein, in some embodiments, the pacing monitor assembly 28 is configured to determine whether at least one of (i) phrenic nerve pacing, and (ii) cryoablation, is occurring at any given time. Further, in certain alternative embodiments, based on the monitor output from the pacing monitor assembly 28 as to whether one or both of these processes are occurring, the control system 14 can then activate the safety system 40, which can provide an alert (e.g., a visual, audio and/or haptic alert) to the operator and can terminate the cryoablation process, e.g., flow of the cryogenic fluid 30 to the balloon catheter 18, under certain circumstances, as provided herein.

As provided herein, in various embodiments, the pacing detector 36 directly and automatically monitors or senses movement of the diaphragm 42 of the patient 12 to detect when phrenic nerve pacing has begun. As such, the pacing detector 36 can also be referred to as an automated pacing detector. The specific type of pacing detector 36 that is used in the pacing monitor assembly 28 can be varied. In one embodiment, the pacing detector 36 can include an accelerometer. Alternatively, the pacing detector 36 can include a strain gauge. Still alternatively, the pacing detector 36 can include a compound muscle action potential (CMAP) signal detector. In other embodiments, the pacing detector 36 can include any other suitable type of automated movement detector or monitor.

In certain embodiments, the pacing detector 36 can be positioned extracorporeal to the patient 12 and/or near the diaphragm 42 of the patient 12. The pacing detector 36 can detect, determine and/or otherwise monitor movement of the diaphragm 42, and can detect changes in such movement. In some embodiments, the pacing detector 36 can generate any relevant movement information, e.g., the monitor output, and can transmit or otherwise send any relevant movement information to the handle assembly 20 and/or the control system 14 for further assimilation and/or analysis. In the embodiment illustrated in FIG. 1, the pacing detector 36 is configured to transmit or otherwise send the monitor output to the handle assembly 20. In one such embodiment, the handle assembly 20 can then transmit or otherwise send the monitor output to the control system 14. The control system 14 can then determine whether a change in the movement of the diaphragm 42 (i.e. frequency, amplitude, etc.) is greater or less than a predetermined percentage. In so doing, the control system 14 can determine whether movement of the diaphragm 42 of the patient 12 is typical (within a normal range) or atypical (outside of a normal range). The monitor output, e.g., as evaluated by the control system 14, can then be transmitted or otherwise sent to the safety system 40.

The ablation detector 38 detects when cryoablation, e.g., flow of cryogenic fluid 30 to the balloon catheter 18, is occurring. The specific type of ablation detector 38 that is used in the pacing monitor assembly 28 can be varied. In one embodiment, the ablation detector 38 detects initiation of the cryoablation process once the flow of cryogenic fluid 30 is activated and/or once a command for the flow of cryogenic fluid 30 has been given. It is recognized that although the ablation detector 38 illustrated in FIG. 1 is shown within the control console 22 and adjacent to the control system 14, the ablation detector 38 can equally and effectively be positioned in any other suitable location, e.g., in or on the handle assembly 20, or any other location. In various embodiments, and under certain circumstances, the safety system 40 can receive the monitor output and based at least in part on the monitor output can selectively provide an alert to the operator and/or terminate the cryoablation process, e.g. stop the flow of cryogenic fluid 30 to the balloon catheter 18. For example, in some such embodiments, the safety system 40 only provides an alert to the operator and/or terminates the cryoablation process if the monitor output shows that the movement of the diaphragm is atypical. The specific design of the safety system 40 and the specific type of alert that may be provided by the safety system 40 can be varied. In one embodiment, the safety system 40 can include an audible alert (i.e. alarm) that is sounded. In another embodiment, the safety system 40 can include a shut-off valve that closes in order to terminate the flow of cryogenic fluid 30 to the balloon catheter 18. In still another embodiment, the safety system 40 can provide a visual alert to the operator that is visible on the graphical display 24. In yet another embodiment, the safety system 40 can provide a haptic alert to the operator, e.g., by vibrating the handle assembly 20. However, it is appreciated that the safety system 40 can include any suitable means and/or method for alerting the operator and terminating the cryoablation process. Additionally, it is recognized that although the safety system 40 illustrated in FIG. 1 is shown within the control console 22 and adjacent to the control system 14, the safety system 40 can equally and effectively be positioned in any other suitable location, e.g., in or on the handle assembly 20, or any other location.

In certain embodiments, the safety system 40 will only provide an alert to the operator or terminate the cryoablation process when movement of the diaphragm 42 of the patient 12 is atypical, if both (i) phrenic nerve pacing is occurring, and (ii) cryoablation is occurring. In an alternative embodiment, the safety system 40 will only provide an alert to the operator or terminate the cryoablation process when movement of the diaphragm 42 of the patient 12 is atypical, if at least one of (i) phrenic nerve pacing is occurring, and (ii) cryoablation is occurring.

Figure 2:
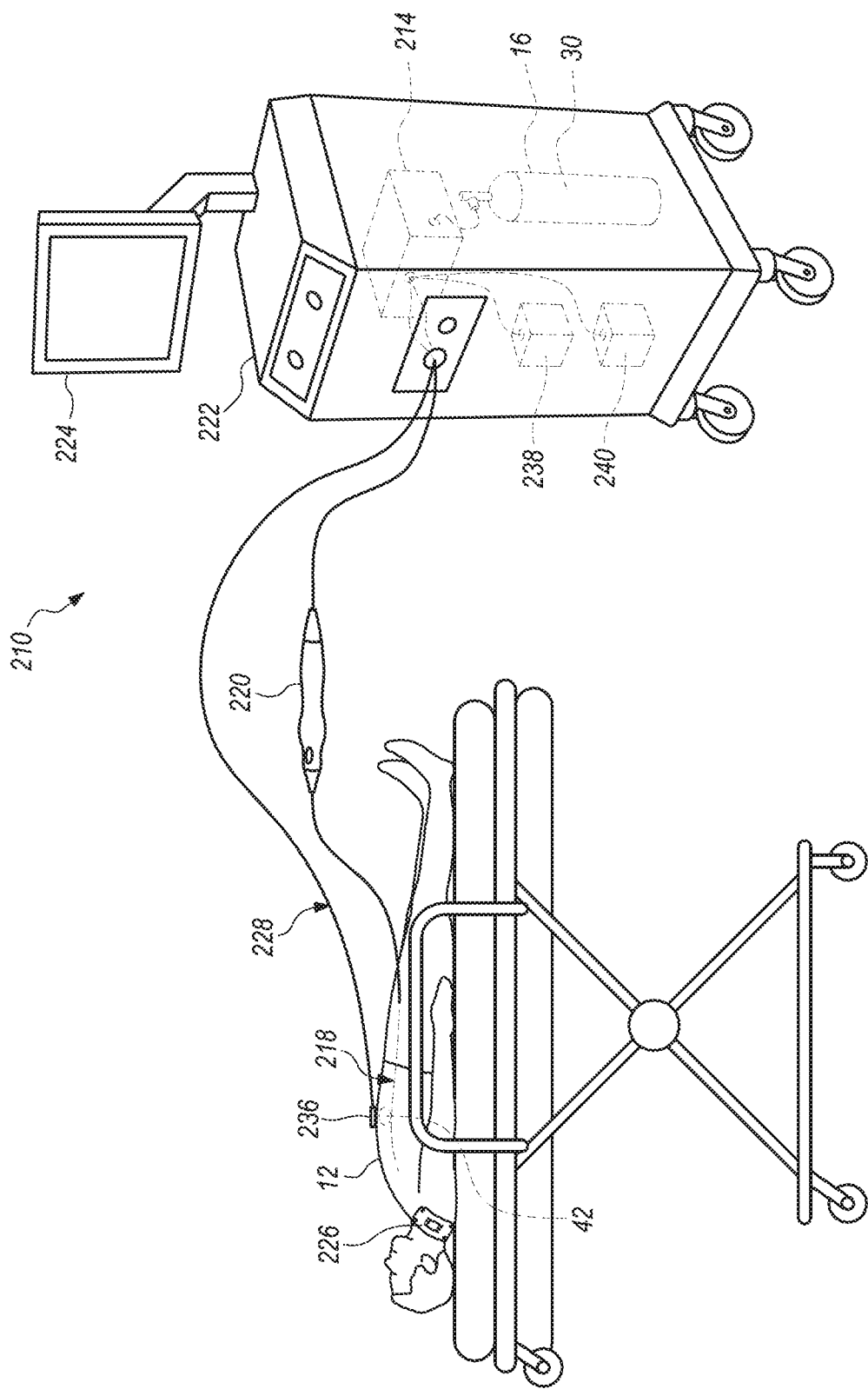
FIG. 2 is a simplified schematic side view illustration of a patient and another embodiment of a cryogenic balloon catheter system including the phrenic nerve stimulator and another embodiment of the phrenic nerve pacing monitor assembly.

FIG. 2 is a simplified schematic side view illustration of another embodiment of a cryogenic balloon catheter system 210 for use with a patient 12, which can be a human being or an animal. As illustrated in FIG. 2, the cryogenic balloon catheter system 210 is substantially similar in design and functioning to the cryogenic balloon catheter system 10 illustrated and described above in relation to FIG. 1 For example, the cryogenic balloon catheter system 210 again includes one or more of a control system 214, a fluid source 216, a balloon catheter 218, a handle assembly 220, a control console 222, a graphical display 224, a phrenic nerve stimulator 226, and a phrenic nerve pacing monitor assembly 228 that are similar in design and functioning to the corresponding components of the cryogenic balloon catheter system 10 illustrated and described above in relation to FIG. 1. Additionally, the phrenic nerve pacing monitor assembly 228 again includes one or more of a pacing detector 236, an ablation detector 238, and a safety system 240 that are similar in design and functioning to the corresponding components of the phrenic nerve pacing monitor assembly 28 illustrated and described above in relation to FIG. 1. Stated in another manner, unless otherwise described herein below, similar structures operate substantially similarly to those previously shown and described.

However, in the embodiment illustrated in FIG. 2, the pacing detector 236 is configured to provide monitor output in a slightly different manner than in the previous embodiment. As above, the (automated) pacing detector 236 directly and automatically monitors or senses movement of the diaphragm 42 of the patient 12 to detect when phrenic nerve pacing has begun. In the embodiment illustrated in FIG. 2, the pacing detector 236 can again be positioned extracorporeal to the patient 12 and/or near the diaphragm 42 of the patient 12. Contrary to the previous embodiment, however, the pacing detector 236 as illustrated in FIG. 2 is configured to transmit or otherwise send the monitor output directly to the control system 214 (and not indirectly via the handle assembly 220). The control system 214 can then determine whether a change in the movement of the diaphragm (i.e. frequency, amplitude, etc.) is greater or less than a predetermined percentage. In so doing, the control system 214 can determine whether movement of the diaphragm 42 of the patient 12 is typical (within a normal range) or atypical (outside of a normal range).

Figure 3:
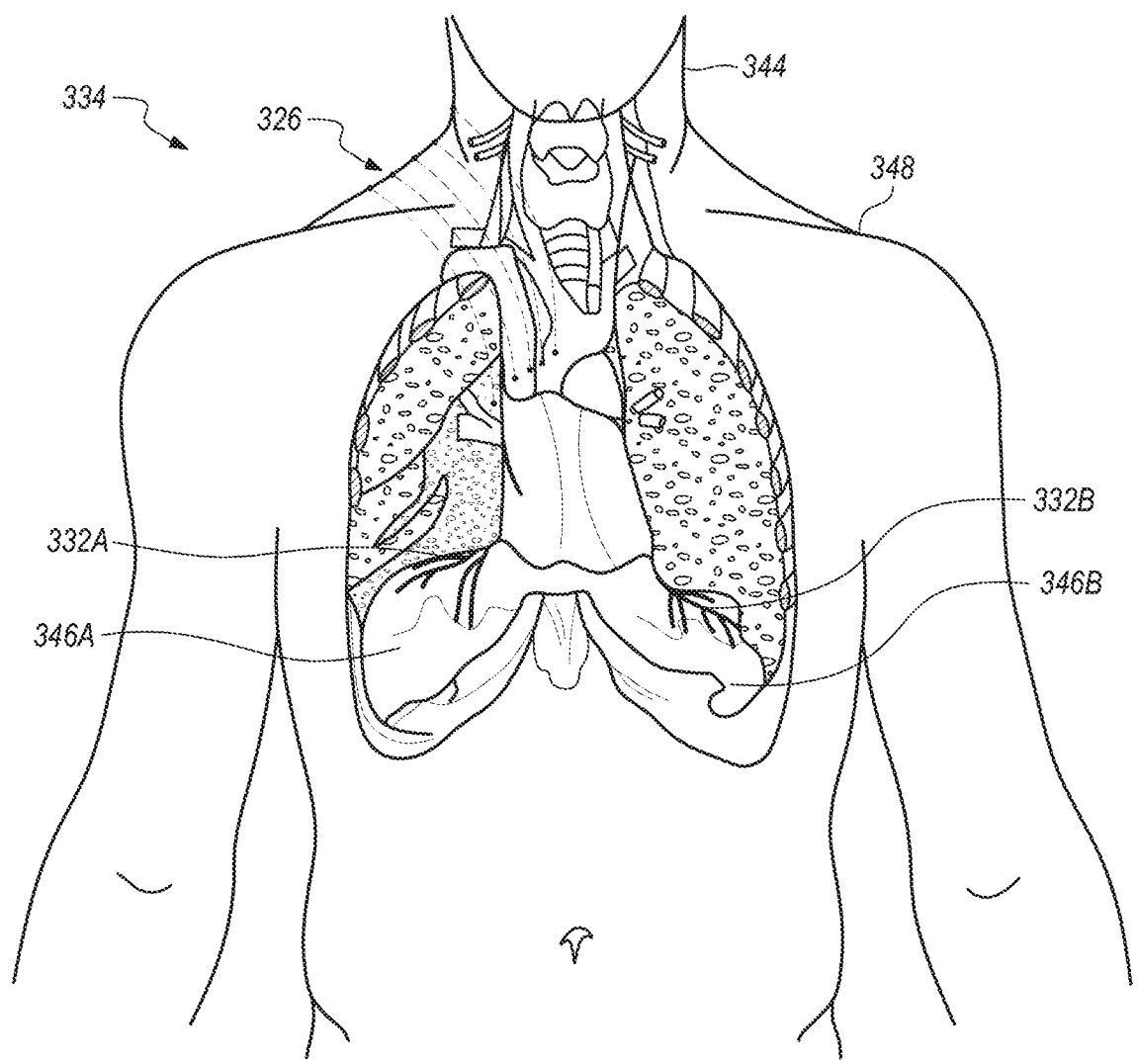
FIG. 3 is a simplified front view of a portion of the human body, and one embodiment of the phrenic nerve stimulator having features of the present invention that is positioned on the human body.

FIG. 3 is a simplified front view of a portion of the human body 334 (or human anatomy), e.g., the body 334 of the patient 12 (as illustrated, for example, in FIG. 1). In particular, FIG. 3 illustrates a first (right) phrenic nerve 332A that extends from the area of the neck 344, i.e. from the 3rd, 4th, and 5th cervical nerves in the neck 344, to a first (right) diaphragm 346A; and a second (left) phrenic nerve 332B that extends from the area of the neck 344 to a second (left) diaphragm 346B. As noted above, the phrenic nerves 332A, 332B are very important to the proper functioning of the human body 334 as the phrenic nerves 332A, 332B stimulate movement of the diaphragm 346A, 346B to help facilitate breathing.

FIG. 3 also illustrates an embodiment of a phrenic nerve stimulator 326 (illustrated in dashed lines, and also referred to herein simply as a "nerve stimulator") having features of the present invention that is positioned on the human body 334. As provided herein, the specific placement or positioning of the nerve stimulator 326 is designed to provide desired stimulation to the phrenic nerve 332A, 332B.

As provided herein, the phrenic nerve stimulator 326 is utilized, e.g., during a cardiac ablation procedure, to stimulate the phrenic nerve 332A, 332B from outside the body 334, i.e. in an extracorporeal manner. Although the placement of the nerve stimulator 326 may vary slightly, as shown in FIG. 3, the nerve stimulator 326 is designed for easy and accurate placement in the region behind the neck 344 and around the anterior of the living body in proximity to the shoulder 348. Additionally, as provided herein, the nerve stimulator 326 is configured to provide an electromagnetic field 750 (illustrated in FIG. 7) encompassing the phrenic nerve 332A, 332B such that the nerve stimulator 326 may stimulate the phrenic nerve 332A, 332B using pulsed voltage or current of a frequency and magnitude suitable for pacing the phrenic nerve 332A, 332B. In particular, in various embodiments, the nerve stimulator 326 includes a plurality of electrodes 452 (illustrated, for example, in FIG. 4) that are arranged in one or more bipolar electrode pairs in order to provide such an electromagnetic field 750. With this design, by providing desired stimulation to the phrenic nerve 332A, 332B from outside the living body 334, the nerve stimulator 326 is able to provide a relatively easy and cost-effective means to inhibit unintended injury to the phrenic nerve 332A, 332B that may otherwise occur during a cardiac ablation procedure.

Figure 4:
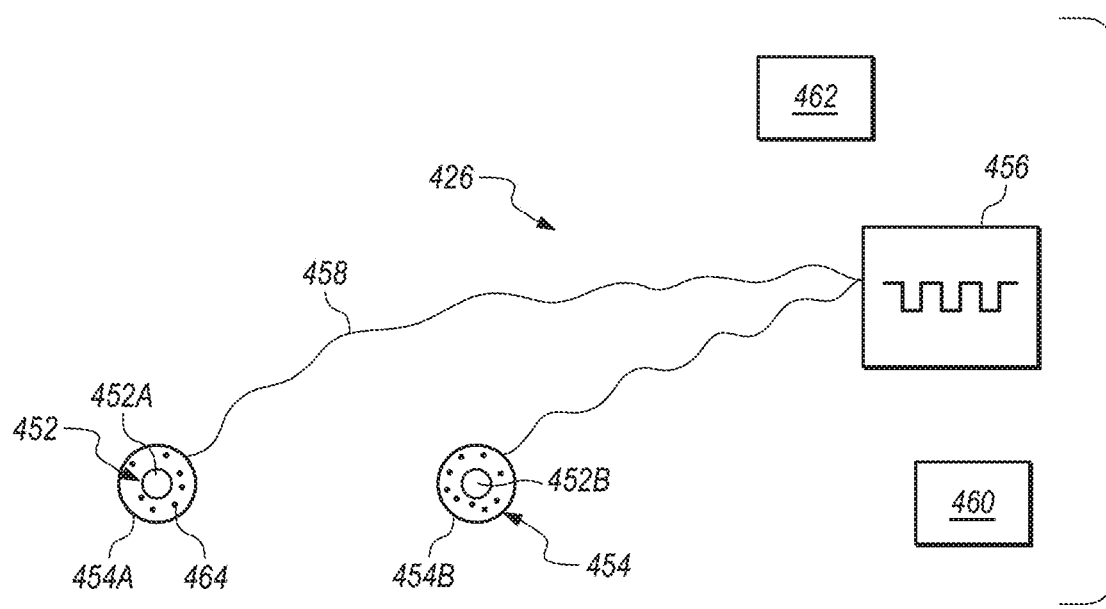
FIG. 4 is a simplified schematic view illustration of an embodiment of the phrenic nerve stimulator.

FIG. 4 is a simplified schematic view illustration of an embodiment of the phrenic nerve stimulator 426 that can be used to selectively stimulate the phrenic nerve 332A, 332B (illustrated in FIG. 3), i.e. during a cardiac ablation procedure or during another type of procedure.

The design of the nerve stimulator 426 can be varied. In certain embodiments, as shown in FIG. 4, the nerve stimulator 426 can include a plurality of electrodes 452, a plurality of patches 454, a pulse generator 456, an electrical connection assembly 458 that electrically couples the electrodes 452 to the pulse generator 456, a controller 460, and a power source 462. Alternatively, the nerve stimulator 426 can include more components or fewer components than those specifically illustrated in FIG. 4, and/or the nerve stimulator 426 can have another suitable design.

In the embodiment illustrated in FIG. 4, each of the plurality of electrodes 452 is secured to one of the plurality of patches 454. More specifically, the nerve stimulator 426 includes a first electrode 452A that is secured to a first patch 454A, and a second electrode 452B that is secured to a second patch 454B. The electrodes 452A, 452B are configured to operate as a bipolar pair of electrodes. Although this embodiment only illustrates the inclusion of a single pair of electrodes 452A, 452B, it is appreciated that the nerve stimulator 426 can include any suitable number of pairs of electrodes 452A, 452B. Necessary wiring is also provided for purposes of electrically connecting the electrodes 452A, 452B to the skin of the human body 334 (illustrated in FIG. 3).

Additionally, in certain embodiments, the nerve stimulator 426 may further include a third (reference) electrode (not shown) that can be used in conjunction with each pair of electrodes 452A, 452B. In particular, in such embodiments, an external reference electrode may also be attached to the human body 334, but placed somewhat further away from the phrenic nerve 332A, 332B than the bipolar stimulation electrodes 452A, 452B.

The shape of the electrodes 452A, 452B is selected to maximize electrode-to-skin contact. Additionally, the electrode 452A, 452B is designed to protrude from the surface of the patch 454A, 454B to ensure better skin contact. The designed electrode contact area maximizes electrode-to-skin contact, such that non-conductive matter, such as human hair, does not interfere with creating the desired electromagnetic field 750 (illustrated in FIG. 7). In certain non-exclusive embodiments, the shape of the electrodes 452A, 452B may be spherical, rectangular, or circular. Additionally, the electrodes 452A, 452B can be made from any conductive metal such as stainless steel or other commonly used metals for body surface electrocardiogram (ECG) mapping.

The patches 454A, 454B can be any suitable size and shape. For example, in the embodiment illustrated in FIG. 4, the patches 454A, 454B are substantially circular-shaped. Alternatively, the patches 454A, 454B can be substantially square-shaped, rectangular-shaped, oval-shaped, or another suitable shape. Additionally, the patches 454A, 454B have an adhesive 464 that is applied to one side of the patch 454A, 454B for purposes of enabling the patches 454A, 454B, and thus the electrodes 542A, 452B, to be effectively secured to the skin of the patient 12 (illustrated, for example, in FIG. 1). In one embodiment, the patches 454A, 454B further include a removable film covering (not shown) for covering the adhesive 464 prior to use. Thus, in such embodiment, when it is desired to utilize the nerve stimulator 426, the film covering can be removed from the patches 454A, 454B so that the adhesive 464 is exposed, and so that the patches 454A, 454B and electrodes 452A, 452B can be secured to the skin of the patient 12 in appropriate locations. As provided in greater detail herein below, the patches 454A, 454B, and thus the electrodes 452A, 452B, can be applied to the human body 334 so that they contain the phrenic nerve 332A, 332B within an electromagnetic field 750 created by the pulse generator 456, electrical conductors, and the electrodes 452A, 452B of the nerve stimulator 426. More particularly, in various embodiments, the spacing between bipolar electrodes 452A, 452B is minimized to provide the best electrical field density to ensure phrenic nerve capture and stimulation.

The pulse generator 456 can have any suitable design. The pulse generator 456 is configured to transmit stimulatory energy to each of the electrodes 452A, 452B. More specifically, the pulse generator 456 is electrically connected to the electrodes 452A, 452B via the electrical connection assembly 458, e.g., a plurality of wires, such that pulses of energy that are generated by the pulse generator 456 are easily transmitted to the electrodes 452A, 452B. In one application, the stimulatory energy transmitted from the pulse generator 456 is used to apply energy to one electrode 452A while the other electrode 452B in the matched pair serves as the return path.

In some embodiments, the pulse generator 456 may be secured to and/or incorporated into the patches 454A, 454B with the electrodes 452A, 452B, and powered with a power source 462 such as a battery. Alternatively, in other embodiments, the pulse generator 456 may be an external pulse generator such as a cardiac pacing unit, that is external to and spaced apart from the patches 454A, 454B. A connector assembly can be used to electrically connect the electrode to an external stimulator, such as the external cardiac pacing device.

The controller 460 controls the overall operation of the nerve stimulator 426. The controller 460, in conjunction with the power source 462, operates and/or supplies electrical power via the pulse generator 456 to the electrode pair 452A, 452B for delivering an electrical signal to the phrenic nerve 332A, 332B. In some embodiments, the controller 460 may be designed for placement external to the human body 334. Alternatively, the controller 460 may also be placed integral along with the electrode pair 452A, 452B within or secured to the patches 454A, 454B. The electrode pair 452A, 452B may be connected to the controller 460 by any suitable means, including the use of wires, leads and/or flex circuits. Additionally, the internal or external controller 460 may be powered by the power source 462 (e.g., a battery which may be rechargeable) or an external power supply.

During operation of the nerve stimulator 426, the controller 460 may be programmed to adjust various parameters of the electrical signal, including pulse width, frequency, voltage, current amplitude, duration, pulse train length, and/or pulse waveform. Such parameters will vary depending upon the particular anatomy and physical characteristics of the living body 334 as well as the course of the phrenic nerve 332A, 332B through the living body 334. Higher energy levels may be needed for stimulation of the phrenic nerve 332A, 332B using the nerve stimulator 426 according to the present invention as opposed to an intravascular site, as is practiced today. For example, the voltage may be selected from a range of 0.1 to 50 V, pulse width may be selected from a range of 100-10,000 µs per phase, average pulse frequency may be selected from a range of 2-200 Hz, and current may be selected from a range of 0.1 µA-30 mA. These parameters are exemplary, but actual stimulation parameters may vary significantly. Programming of the controller 460 may also include activation or deactivation of individual or combinations of electrodes 452A, 452B within an electrode array and the selection of the direction of the current by selecting which activated electrode(s) are to act as the anode and which are to act as the cathode.

Additionally, the electrical signal may be monophasic, biphasic, multiphasic, etc. Further, the controller 460 may be programmed to be unipolar, defined as the flow of current from a stimulating electrode(s) at the site of desired nerve stimulation to a reference ground, or bipolar stimulation, where the stimulating current flows between closely spaced anode and cathode electrodes. The electrical signal may be current-controlled, voltage-controlled, or a combination of both. The electrical signal may be pulsatile, episodic, continuous, cyclic, phasic, in clusters, intermittent, upon demand by a user, or preprogrammed to respond to a sensor. The controller 460 may operate any number or combination of electrodes and may make any electrode in an electrode array either an anode or cathode depending on the application and biologic response.

In certain embodiments, the nerve stimulator 426 can further include a feedback mechanism (not shown) for adjusting the electrical signal based on one or more of the cardiovascular or diaphragmatic parameters of the living body 334. For this purpose, the nerve stimulator 426 may sense diaphragm movement rate via the stimulating electrodes 452A, 452B or further include a sensor(s), e.g., the pacing detector 36 illustrated in FIG. 1, for measuring a diaphragm movement parameter of a living body 10. Information about the parameter is fed to the controller 460, which is then programmed to adjust the stimulation signal being applied to the electrode 452A, 452B in response to the information about the diaphragm movement parameter. Alternatively, the controller 460 may alert the user in response to information. Additional non-limiting sources of physiological parameter feedback to the nerve stimulator 426 or controller 460 include sensed physiologic parameter input from a separate implanted or external physiologic monitor which receives its inputs from physiologic sensors. Sensor inputs to the nerve stimulator 426 can be via either hardwired or radio frequency telemetry.

In operation, physiologic sensor inputs to the controller 460 can be obtained from either the controller's own integrated physiologic sensor and or any combination of the following; radio frequency or hardwired sensor inputs an intravascular or implanted physiologic sensor module(s), or radio frequency or hardwired inputs from an external physiologic sensor module(s). The analog or digital signal(s) from the sensor is converted to digital form and can be conditioned through a digital signal processor (DSP). A microprocessor, e.g., that is provided within the controller 460 or separate from the controller 460, then receives the sensor inputs from the DSP. The microprocessor and/or the controller 460 uses this information in an algorithm to analyze the diaphragmatic movement parameter of the living body 334. A microprocessor then outputs instructions to the Nerve Stimulation Circuit which in turn generates the electrical signal to be applied to the electrode or electrodes 452A, 452B. The electrical control signals are converted to stimulation waveforms and delivered through output drivers to the selected electrode wires and to the electrodes 452A, 452B within the nerve stimulator 426. The stimulating waveform can be configured to a selected frequency, pulse width and duty cycle. The stimulation waveforms are then applied to the living body 334 at the stimulation site.

A non-limiting example of an external nerve stimulator 426, such as provided herein, includes a hardwired communications port or a wireless means, to receive incoming operational and patient specific physiologic sensor inputs, and processes the inputs using a closed loop control algorithm to output control signals to the nerve stimulation circuit which in turn outputs stimulation pulses to output drivers that deliver the pulse to selected electrode pairs within the nerve stimulator 426.

Figure 5:
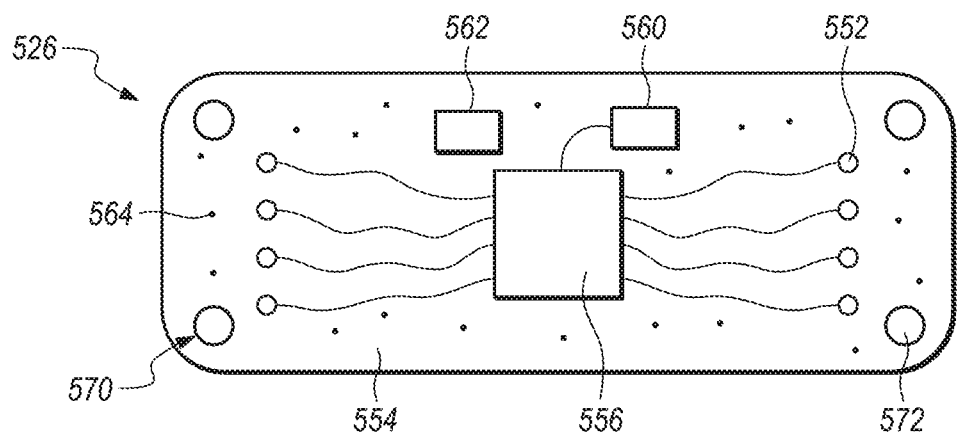
FIG. 5 is a simplified schematic view illustration of another embodiment of the phrenic nerve stimulator.

FIG. 5 is a simplified schematic view illustration of another embodiment of the phrenic nerve stimulator 526. The nerve stimulator 526 is somewhat similar to what was illustrated and described above in relation to FIG. 4. For example, the nerve stimulator 526 again includes a pulse generator 556, a controller 560 and a power source 562 that operate in a somewhat similar manner as what was described above. Accordingly, a detailed description of the operation of such components will not be repeated herein. Additionally, the nerve stimulator 526 again includes a plurality of electrodes 552 (arranged in bipolar electrode pairs) that function in a similar manner to what was described above. However, in this embodiment, the overall design and layout of the components of the nerve stimulator 526 is somewhat different than in the previous embodiment.

For example, as shown in FIG. 5, in this embodiment, the nerve stimulator 526 includes a plurality of pairs of electrodes 552 that are all secured to a single patch 554. It is understood that the number of electrode pairs 552 can be varied to suit the specific requirements of the nerve stimulator 526. In one embodiment, as illustrated in FIG. 5, the nerve stimulator 526 can include four bipolar electrode pairs 552. Alternatively, the nerve stimulator 526 can include greater than four or less than four bipolar electrode pairs 552.

It is anticipated that in such an embodiment with multiple pairs of electrodes 552 incorporated into the nerve stimulator 526, the nerve stimulator 526 can be positioned on the human body 334 (illustrated in FIG. 3) in a less precise manner while still providing effective phrenic nerve capture and pacing. In such embodiments, an algorithm may be employed within the controller 560 to sequence through electrode pairs 552 or potential pairs to select the best electrode combination offering the phrenic nerve capture. This may include the electrode pair 552 that provides the lowest stimulatory energy required to achieve phrenic nerve capture.

Additionally, in this embodiment, in addition to the multiple bipolar electrode pairs 552, each of the pulse generator 556, the controller 560 and the power source 562 are also integrally formed within or are secured to the patch 554. The patch 554, and all components integrally formed into or secured to the patch 554, can be appropriately positioned on the body 334 with an adhesive 564 that is provided on one side of the patch 554.

In some embodiments, the patch 554 can be made from a die-cut medical tape or film. The tape or film and adhesive 564 combination is selected based on its ability to stick to skin and to ensure good electrical contact between the electrodes 552 and the skin. The shape of the patch 554 is carefully controlled using precision die-cutting techniques so that it is compact in size and facilitates accurate placement on the body 334 to align integrated electrodes 552 near the phrenic nerve 332A, 332B (illustrated in FIG. 3). Examples of suitable tape materials include 3M 1504, 3M 1520, 3M 1603, 3M 1776, 3M 2475 (3M Medical Specialties). There are also other suitable tapes available.

Further, as illustrated in this embodiment, the nerve stimulator 526 can also incorporate an alignment system 570 that ensures that the nerve stimulator 526 is accurately positioned when it is adhered to the skin of the body 334. For example, in one such embodiment, the alignment system 570 can include a plurality of fiducial features, such as holes 572 that are cut into the patch 554, to guide accurate placement of the patch 554. Such features could also include notches that are formed at the edges of the patch 554. Such fiducial features, when the patch 554 is being adhered to the body 334, can be aligned to anatomical landmarks such as visible vertebra, the clavical or collarbone, the top of the shoulder or any other landmarks on the body 334 that help ensure accurate placement of the nerve stimulator 526. The landmarks can also include marks applied to the body 334, using ink for example, applied by the operator on the patient 12 (illustrated in FIG. 1). The marks may be applied to the patient 12 after testing using a pre-placement device, using trial and error to locate the device, at any advantageous anatomical location.

Figure 6A:
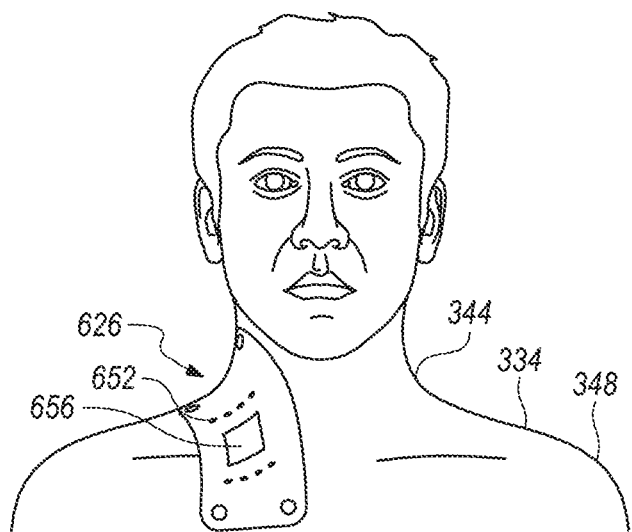
FIG. 6A is a front view illustration of the anatomical location of the phrenic nerve stimulator when placed on the body of the patient.

FIG. 6A is a front view illustrating the anatomical location of the phrenic nerve stimulator 626 when placed on the body 334 of a patient (e.g., the patient 12 illustrated in FIG. 1).

Figure 6B:
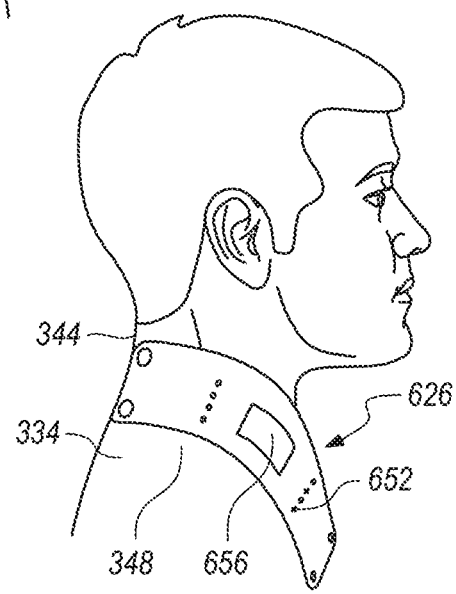
FIG. 6B is a side view illustration of the anatomical location of the phrenic nerve stimulator when placed on the body of the patient.

Additionally, FIG. 6B is a side view of the anatomical location of the phrenic nerve stimulator 626 when placed on the body 334 of the patient 12.

As noted above, when adhering the nerve stimulator 626 to the body 334 of the patient, it is desired that the spacing between bipolar electrodes be minimized to provide the best electric field density possible to ensure phrenic nerve capture and stimulation. Hence, the shape of the nerve stimulator 626 is designed to optimally position the electrodes 652 on either side of and as close as possible to the phrenic nerve 332A, 332B (illustrated in FIG. 3). In other words, the phrenic nerve 332A, 332B is positioned within the electromagnetic field 750 (illustrated in FIG. 7) created by the electrode pair 652, and the distance between the electrodes 652 is minimized to provide a high field density. The particular shape of the nerve stimulator 626 in this embodiment places one electrode 652 from each bipolar electrode pair behind the neck 344, near vertebra C3-C5, and places the other electrode 652 near the front of the shoulder 348. As noted above, there may be more than one set of bipolar electrode pairs 652 to optimize phrenic nerve capture. The phrenic nerve 332A, 332B, placed within the electromagnetic field 750 created by the bipolar electrode pairs 652, is then stimulated by the pulse generator 656. The resulting phrenic nerve stimulation is then monitored by the nerve stimulator 626, an external device, an operator or the combination of a device and operator to assess effect.

Figure 7:
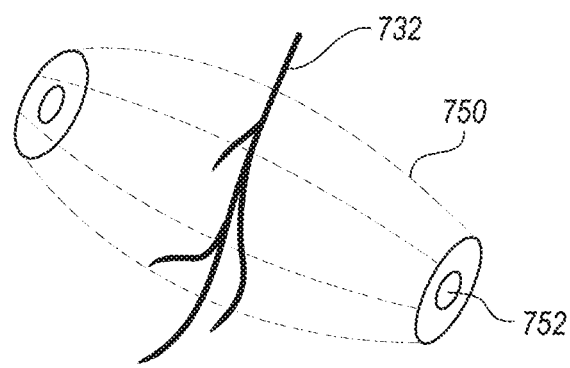
FIG. 7 is a simplified schematic view illustration of a phrenic nerve within a stimulatory electromagnetic field generated by the phrenic nerve stimulator.

FIG. 7 is a simplified schematic view illustration of a phrenic nerve 732 within a stimulatory electromagnetic field 750 generated by the phrenic nerve stimulator, e.g., the phrenic nerve stimulator 326 illustrated in FIG. 3, and the electrodes 724 included therein.

It is understood that although a number of different embodiments of the phrenic nerve pacing monitor assembly 28, 228, and the phrenic nerve stimulator 326 have been illustrated and described herein, one or more features of any one embodiment can be combined with one or more features of one or more of the other embodiments, provided that such combination satisfies the intent of the present invention.

While a number of exemplary aspects and embodiments of the phrenic nerve pacing monitor assembly 28, 228, and the phrenic nerve stimulator 326 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

We claim:

1. A cryogenic balloon catheter system for use in a cryoablation procedure, the cryogenic balloon catheter system comprising:
   a cryogenic balloon catheter;
   an external phrenic nerve stimulator configured to selectively stimulates a phrenic nerve of a patient, the phrenic nerve stimulator comprising:
     at least one pair of extracorporeal electrodes;
     a pulse generator electronically connected to the at least one pair of electrodes, configured to transmit stimulatory energy to the at least one pair of electrodes;
     a power source electronically coupled to the pulse generator;
     a controller electronically coupled to the pulse generator, configured to control the operation of the phrenic nerve stimulator; and a patch, wherein the at least one pair of electrodes, the pulse generator, the power source, and the controller are disposed on the patch, and wherein the patch is configured to be positioned extracorporeally on the patient so that the at least one pair of electrodes are aligned with the phrenic nerve of the patient; and a phrenic nerve pacing monitor assembly comprising:
a pacing detector that directly monitors movement of the diaphragm of the patient to detect when phrenic nerve pacing is occurring, the pacing detector generating monitor output based on the movement of the diaphragm of the patient; and
a safety system that receives the monitor output and based at least in part on the monitor output selectively provides an alert when movement of the diaphragm of the patient is atypical, the safety system being configured to provide the alert only while at least one of phrenic nerve pacing is occurring or cryoablation is occurring.

2. The cryogenic balloon catheter system of claim 1, wherein the at least one pair of electrodes includes a first electrode and a second electrode that are arranged in a bipolar electrode pair.

3. The cryogenic balloon catheter system of claim 2, wherein the first electrode is configured to be positioned near vertebra C3-C5 of the patient and the second electrode is configured to be positioned near a front of a shoulder of the patient.

4. The cryogenic balloon catheter system of claim 2, wherein the first electrode is configured to be positioned extracorporeally near a neck of the patient and the second electrode is configured to be positioned extracorporeally near a shoulder of the patient.

5. The cryogenic balloon catheter system of claim 2, wherein the safety system is further configured based at least in part on the monitor output to selectively terminate the cryoablation procedure when movement of the diaphragm of the patient is atypical, the safety system being configured to terminate the cryoablation procedure only while at least one of phrenic nerve pacing is occurring or cryoablation is occurring.

6. The cryogenic balloon catheter system of claim 5, wherein the pacing detector automatically monitors movement of the diaphragm of the patient, and automatically generates the monitor output based on the movement of the diaphragm of the patient.

7. The cryogenic balloon catheter system of claim 6, wherein the safety system includes a shut-off valve that selectively closes to terminate the cryoablation procedure.

8. The phrenic nerve stimulator of claim 1, wherein the bipolar electrode pair receives the stimulatory energy from the pulse generator and provides an electromagnetic field to encompass the phrenic nerve of the patient.

9. The cryogenic balloon catheter system of claim 1, wherein the single patch contains an alignment system including a plurality of holes that are cut into the single patch to guide accurate placement of the single patch.

10. A method for monitoring movement of a diaphragm of a patient during a cryoablation procedure, the method comprising:
positioning a phrenic nerve stimulator extracorporeally on a skin surface of the patient, wherein the phrenic nerve stimulator is configured to selectively stimulate a phrenic nerve of the patient and includes:
at least one pair of electrodes;
a pulse generator electronically connected to the at least one pair of electrodes, configured to transmit stimulatory energy to the at least one pair of electrodes;
a power source electronically coupled to the pulse generator;
a controller electronically coupled to the pulse generator, configured to control the operation of the phrenic nerve stimulator; and
a patch, wherein the at least one pair of electrodes, the pulse generator, the power source, and the controller are disposed on the patch, and wherein the patch is configured to be positioned extracorporeally on the patient so that the at least one pair of electrodes are aligned with the phrenic nerve of the patient;
actively pacing the phrenic nerve of the patient using the phrenic nerve stimulator;
directly monitoring movement of the diaphragm of the patient with a pacing detector to detect when phrenic nerve pacing is occurring;
generating monitor output with the pacing detector based on the movement of the diaphragm of the patient;
receiving the monitor output with a safety system; and
selectively providing an alert with the safety system based at least in part on the monitor output when movement of the diaphragm of the patient is atypical, the safety system being configured to provide the alert only while at least one of phrenic nerve pacing is occurring or cryoablation is occurring.

11. The method of claim 10, further comprising selectively terminating the cryoablation procedure with the safety system based at least in part on the monitor output when movement of the diaphragm of the patient is atypical, the safety system being configured to terminate the cryoablation procedure only while at least one of phrenic nerve pacing is occurring or cryoablation is occurring.

12. The method of claim 10, further comprising actively stimulating the phrenic nerve during the application of cryoablation energy.

13. The method of claim 12, wherein actively stimulating the phrenic nerve includes:
arranging a first electrode and a second electrode in a bipolar electrode pair;
positioning the first electrode near vertebra C3-C5 of the patient;
positioning the second electrode near a front of a shoulder of the patient; electrically coupling a pulse generator to the bipolar electrode pair; and transmitting stimulatory energy from the pulse generator to the bipolar electrode pair.

14. The method of claim 12, wherein actively stimulating the phrenic nerve includes:
arranging a first electrode and a second electrode in a bipolar electrode pair;
positioning the first electrode extracorporeally near a neck of the patient; positioning the second electrode extracorporeally near a shoulder of the patient; electrically coupling a pulse generator to the bipolar electrode pair; and transmitting stimulatory energy from the pulse generator to the bipolar electrode pair.

* * * * *